United States Patent
Dwivedi et al.

(10) Patent No.: US 8,958,620 B2
(45) Date of Patent: Feb. 17, 2015

(54) REGION OF INTEREST DEFINITION IN CARDIAC IMAGING

(75) Inventors: Shekhar Dwivedi, Uttar Pradesh (IN); Manish Kumar Sharma, Bangalore (IN); Narayan Ayyakad Krishnan, Bangalore (IN); Yogish Mallya, Bangalore (IN)

(73) Assignee: Koninklijke Philips N.V., Eindhoven (NL)

( * ) Notice: Subject to any disclaimer, the term of this patent is extended or adjusted under 35 U.S.C. 154(b) by 302 days.

(21) Appl. No.: 13/580,166

(22) PCT Filed: Feb. 8, 2011

(86) PCT No.: PCT/IB2011/050533
§ 371 (c)(1),
(2), (4) Date: Aug. 21, 2012

(87) PCT Pub. No.: WO2011/110959
PCT Pub. Date: Sep. 15, 2011

(65) Prior Publication Data
US 2012/0321153 A1    Dec. 20, 2012

Related U.S. Application Data

(60) Provisional application No. 61/311,406, filed on Mar. 8, 2010.

(51) Int. Cl.
*G06K 9/00* (2006.01)
*G06T 7/00* (2006.01)
*A61B 6/00* (2006.01)

(52) U.S. Cl.
CPC .............. *G06T 7/0081* (2013.01); *A61B 6/469* (2013.01); *A61B 6/503* (2013.01); *G06T 7/0012* (2013.01);

(Continued)

(58) Field of Classification Search
None
See application file for complete search history.

(56) References Cited

U.S. PATENT DOCUMENTS

| | | | |
|---|---|---|---|
| 5,404,426 A * | 4/1995 | Usami et al. | 345/420 |
| 5,509,084 A | 4/1996 | Tanaka | |

(Continued)

FOREIGN PATENT DOCUMENTS

| | | |
|---|---|---|
| WO | 2006105071 A1 | 10/2006 |
| WO | 2008002797 A2 | 1/2008 |
| WO | 2008150945 A2 | 12/2008 |

OTHER PUBLICATIONS

Domenichelli, S., et al. "Quantitative cardiac dynamic imaging of small animal PET images using cluster analysis." Computers in Cardiology, 2008. IEEE, 2008.*

*Primary Examiner* — Tahmina Ansari

(57) ABSTRACT

A method for cardiac imaging for determining a myocardial region of interest (ROI) is disclosed. The method includes acquiring functional imaging data of a subject, where the functional imaging data includes at least the myocardium. A ROI encompassing at most the myocardium from the acquired functional imaging data, and diagnostic parameters relating to the myocardium are estimated and quantified based on the determined ROI. In one embodiment, the ROI is determined from a projection image representation utilizing histogram based thresholding and ray casting based localization to determine the extents of the ROI. In another embodiment, the ROI is determined from a volumetric image representation utilizing clustering Manhattan distance based cleaning to determine cardiac angles used for reorienting the left ventricle.

22 Claims, 18 Drawing Sheets

(52) U.S. Cl.
CPC ............... *G06T 2207/10108* (2013.01); *G06T 2207/20104* (2013.01); *G06T 2207/20132* (2013.01); *G06T 2207/20148* (2013.01); *G06T 2207/30048* (2013.01); *A61B 6/507* (2013.01)
USPC ..................................................... 382/131

(56) References Cited

U.S. PATENT DOCUMENTS

| | | | |
|---|---|---|---|
| 5,570,430 A | 10/1996 | Sheehan et al. | |
| 6,065,475 A | 5/2000 | Qian et al. | |
| 6,249,594 B1 | 6/2001 | Hibbard | |
| 7,321,676 B2 | 1/2008 | Lavi et al. | |
| 7,376,253 B2 | 5/2008 | Spreeuwers et al. | |
| 7,400,757 B2 | 7/2008 | Jolly et al. | |
| 7,534,210 B2 * | 5/2009 | Chomas et al. | 600/458 |
| 7,764,813 B2 * | 7/2010 | Lorenz | 382/128 |
| 8,369,590 B2 * | 2/2013 | Wang et al. | 382/128 |
| 8,553,989 B1 * | 10/2013 | Owechko et al. | 382/224 |
| 2006/0069322 A1 * | 3/2006 | Zhang et al. | 600/512 |
| 2006/0253164 A1 * | 11/2006 | Zhang et al. | 607/28 |
| 2007/0058849 A1 * | 3/2007 | Lorenz | 382/131 |
| 2008/0275336 A1 * | 11/2008 | Deschamps et al. | 600/425 |
| 2008/0292169 A1 * | 11/2008 | Wang et al. | 382/131 |
| 2009/0290778 A1 * | 11/2009 | Sun et al. | 382/131 |
| 2012/0321153 A1 * | 12/2012 | Dwivedi et al. | 382/128 |
| 2014/0081132 A1 * | 3/2014 | Dwivedi | 600/425 |

* cited by examiner

REGION OF INTEREST DEFINITION IN CARDIAC IMAGING

CROSS REFERENCE TO RELATED APPLICATIONS

This application claims the benefit of U.S. provisional application Ser. No. 61/311,406 filed Mar. 8, 2010, which is incorporated herein by reference.

The present application relates to medical imaging arts. It finds particular application to region of interest (ROI) definition of myocardial tissue in diagnostic nuclear imaging.

In diagnostic nuclear imaging, a radionuclide distribution is studied as it passes through a patient's bloodstream for imaging the circulatory system or for imaging specific organs that accumulate the injected radiopharmaceutical. In single-photon emission computed tomography (SPECT), for example, one or more radiation detectors, commonly called gamma cameras, are used to detect the radiopharmaceutical via radiation emission caused by radioactive decay events. Typically, each gamma camera includes a radiation detector array and a collimator disposed in front of the radiation detector array. The collimator defines a linear or small-angle conical line of sight so that the detected radiation comprises projection data. If the gamma cameras are moved over a range of angular views, for example over a 180° or 360° angular range, then the resulting projection data can be reconstructed using filtered back-projection, expectation-maximization, or another imaging technique into an image of the radiopharmaceutical distribution in the patient. Advantageously, the radiopharmaceutical can be designed to accumulate in selected tissues to provide preferential imaging of those selected tissues, such as cardiac tissue for the purpose of cardiac imaging.

In many cardiac imaging studies, the left ventricle is of particular interest. As a preliminary step, one wants to define a region of interest of the heart and more specifically the left ventricle. One problem with ROI definition in cardiac imaging studies is that acquired image data exhibits relatively high levels of noise and limited, if any, anatomical information. In cardiac imaging, the activity distribution of the radiopharmaceutical in the vicinity of the heart can be used to estimate myocardial blood flow, regional myocardial blood flow, flow reserve, ejection fraction, or other parameters relevant to diagnosis and treatment. To quantify and estimate these parameters, a myocardial ROI is first identified in the image data. However, accurate quantitative assessment of the myocardial parameters depends, in part, on accurate and repeatable identification of the myocardial ROI.

Typically, the extent and boundaries of the myocardial ROI are manually delineated by a clinician. For example, a clinician may trace the outline of the ROI or mark the individual voxels contained in the ROI using a graphical user interface (GUI). Unfortunately, manual ROI delineation of the extents and boundaries can be a burdensome and time consuming task. Moreover, the outcome of manual ROI delineation tends to be user dependent and prone to non-repeatable results.

Alternatively, multiple modality imaging systems allow for CT, MRI, or the like to provide anatomical information in addition to the myocardial parameters from the nuclear imaging system. The anatomical information can be used to identify the myocardial ROI. The nuclear imaging data which corresponds with the ROI is quantified to determine the diagnostic parameters. However, the anatomical imaging data is susceptible to organ motion and/or low resolution which can present registration errors and poor definition of myocardial ROI.

The present application provides a new and improved system and method that provides accurate, reproducible myocardial ROI definition which overcomes the above-referenced problems and others.

In accordance with one aspect, a method for cardiac imaging is presented. The method includes acquiring functional imaging data of a subject, where the functional imaging data includes at least a region including a myocardium. A region of interest encompassing at most the myocardium is determined from the acquired functional imaging data and diagnostic parameters of the myocardium are estimating based on the determined ROI.

In accordance with another aspect, a diagnostic imaging system is presented. The diagnostic imaging system includes a functional imaging system with at least one detector head for acquiring functional imaging data. A control unit controls the acquisition of the functional image data and/or a position of the detector head. A region of interest processor is programmed to perform the method of cardiac imaging.

In accordance with another aspect, a computer readable storage medium contains instructions, when executed by a computer, causes the computer to carry out the method of cardiac imaging.

One advantage relies in that robustness region of interest definition is improved.

Another advantage relies in that accuracy of parameters extracted from defined region of interests is improved.

Another advantage relies in that little or no user interaction is required to determine the region of interest.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
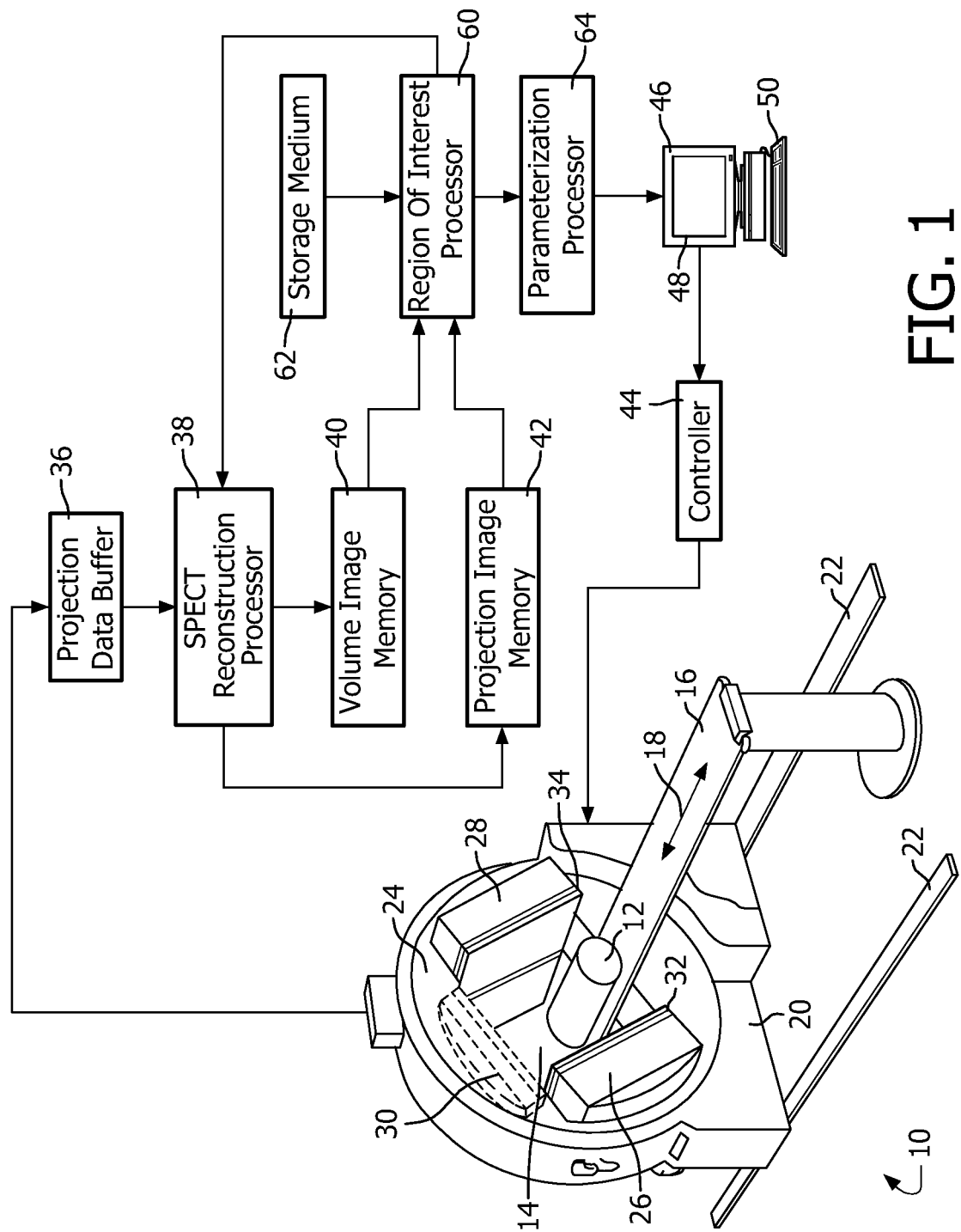
FIG. 1 is a diagrammatic illustration of a diagnostic imaging system with a region of interest processor.

With reference to FIG. 1, a diagnostic imaging system 10 acquires functional imaging data of a subject 12 within an examination region 14. Although a SPECT system is described, it is to be appreciated that other imaging modalities, such as positron emission tomography (PET) or the like are also contemplated. The diagnostic imaging system 10 includes a patient support 16 which is selectively translatable to facilitate in position the subject 12 being imaged or examined at a desired location, e.g. so that the regions of interest are centered about a longitudinal axis 18. Alternatively, an outer gantry 20 is movably mounted on tracks 22 to achieve the desired position of the subject 12 along the longitudinal axis 18.

An inner gantry 24 is rotatably mounted on the outer gantry 20 for stepped or continuous motion. The rotating inner gantry 24 defines the subject receiving examination region 14. One or more detector heads 26, 28, 30 are individually positionable on the rotatable inner gantry 24. The detector heads 26, 28, 30 rotate as a group about the examination region 14 and the subject 12 with the rotation of the rotatably inner gantry 24. The detector heads 26, 28, 30 are radially, circumferentially, and laterally adjustable to vary their distance from the subject 12 and spacing on the rotating gantry 24 to position the detector heads in any of a variety of angular orientations about a central axis.

The detector heads 26, 28, 30 each include an array of radiation detectors such as one of more scintillators that emit a flash of light or photons in response to incident radiation events from the radiopharmaceutical. The scintillator(s) are viewed by an array of photodetectors that receive the light flashes and converts them into electrical signals. Alternatively, an array of direct radiation to electrical pulse detects is also contemplated. Suitable collimation is provided to define projection data, for example a radiation absorbing honeycomb collimator disposed in front of the detector array. A resolver circuit resolves the x, y-coordinates of each received radiation event and the energy of the incident radiation. The relative outputs of the photodetectors are processed and corrected in conventional fashion to generate an output signal indicative of: (i) a position coordinate on the detector head at which each radiation event is received, and (ii) an energy of each event. The energy is used to differentiate between various types of radiation such as multiple emission radiation sources, stray and secondary emission radiation, scattered radiation, transmission radiation, and to eliminate noise.

In SPECT imaging, a projection image representation is defined by the radiation data received at each coordinate on the detector head. In SPECT imaging, a collimator defines the rays along which radiation is received. It should be appreciated that although the illustrated embodiment is described with regard to SPECT imaging, other nuclear imaging modalities are also contemplated, such as positron emission tomography (PET) imaging systems.

In PET imaging, the detector head outputs are monitored for coincident radiation events on two heads. From the position and orientation of the heads and the location on the faces at which the coincident radiation is received, a ray between the coincident event detection points is calculated. This ray defines a line along which the radiation event occurred. In both PET and SPECT, the projection data from a multiplicity of angular orientations of the heads is stored in a projection data buffer 36, and then reconstructed by a reconstruction processor 38 into a transverse volumetric image representation and a projection image representation of the region of interest, which is stored in a volume image memory 40 and a projection image memory 42, respectively. The projection image representation can be a two-dimensional (2D) axial representation of a volume in which the highest attenuation voxels along lines projected through the volume data set are selected. With volumetric image representations, 3D spatial relationships are preserved at the cost of computation time and visualization of smaller features versus projection image representations. Both image representations may include a plurality of transverse slices of image representations along the longitudinal axis 18. The functional imaging system 10 is operated by a controller 44 to perform selected imaging sequences of a selected target area of the subject. A console 46 includes a display unit 48 which displays a graphic user interface (GUI) which a clinician can use with a user input device 50 for controlling the scanner controller 44 to select scanning sequences or protocols The system 10 includes a region of interest (ROI) processor 60 that performs algorithms for defining a region of interest, such as myocardium or the like. In the example of cardiac imaging, it is advantageous to isolate the myocardium from the abdominal region, such as organs like the liver which takes up large amounts of the radiopharmaceutical. The ROI processor 60 receives the reconstructed projection and/or volumetric image representations stored in the respective image memory 40,42 and analyzes the received nuclear data to define the ROI without requiring the aid of an anatomical image or a human operator. An image representation including the ROI and either the projection and/or volumetric image representation can be provided to the display unit 48 for viewing by a clinician. The ROI processor is coupled to a computer readable storage unit 62 that stores received image data, processed image data, algorithms for determining for processing, generating, reconstructing etc., algorithms for determining the ROI, and the like. It is to be appreciated that the projection data buffer 36, volume image memory 40, projection image memory 42, and storage medium 62 maybe part of a single computer readable memory module or implemented as separate modules.

A parameterization processor 64, operatively connected to the ROI processor 62 estimates and quantifies parameters from the ROI such as, in the context of cardiac assessment, myocardial blood flow, regional myocardial blood flow, flow reserve, ejection fraction, and the like. It should be appreciated that the parameters tailored for a specific imaging study, such as cardiac imaging, pulmonary imaging, cerebral imaging, or the like, are also contemplated.

Figure 2:
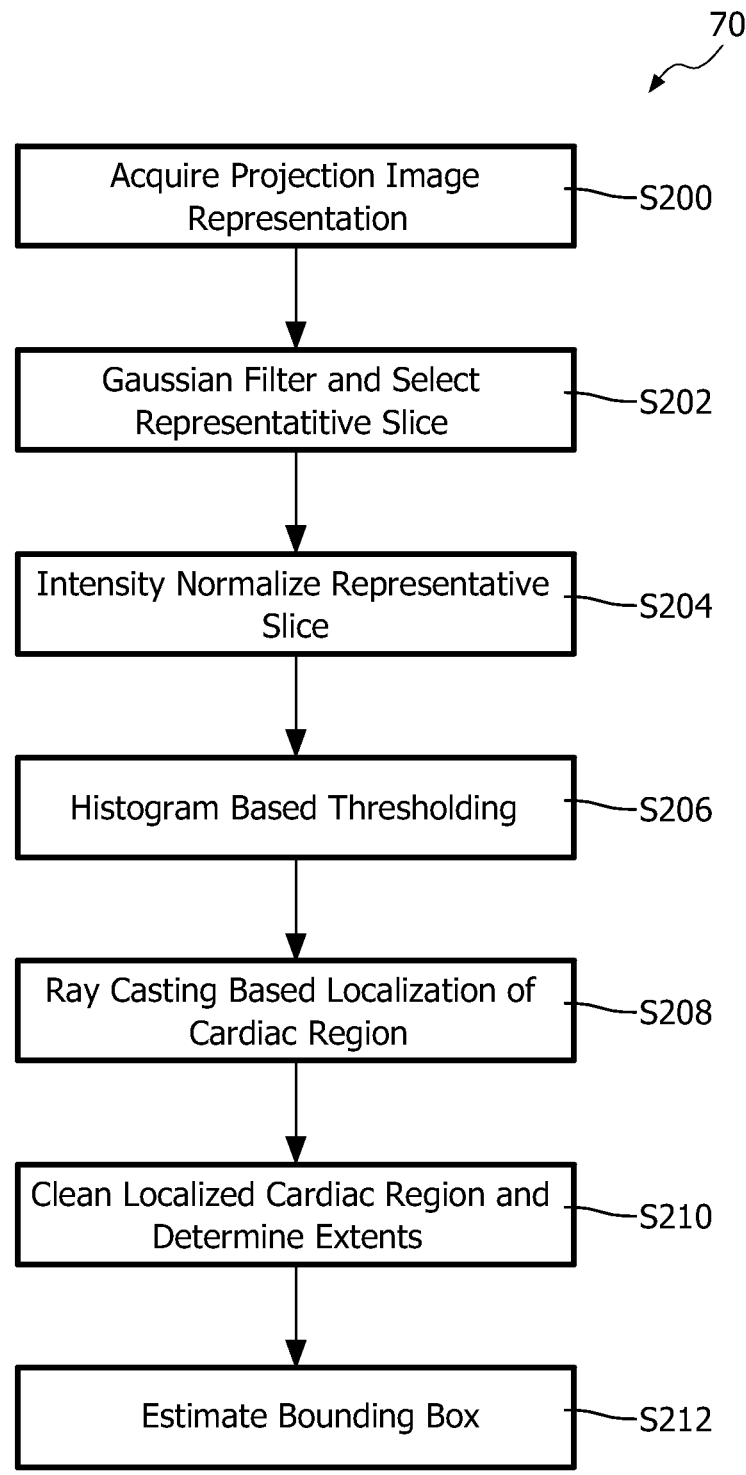
FIG. 2 is a flow diagram representing a method for determining a myocardial region of interest from projection images.

With reference to FIG. 2, in one embodiment, the ROI processor is programmed to perform a method 70 for determining an ROI that at most includes the myocardium and determining the reconstruction extents of the ROI. The ROI processor 60 receives the projection image representation stored on the projection image memory 42 (S200). The 2D images that make up the projection image representation are filtered with a smoothing a filter such as a three-dimensional (3D) Gaussian filter or the like. In the 3D Gaussian filter example, the parameters (e.g. standard deviation, kernel width, kernel height, etc.) can be adapted to the imaging system, patient, or the like. A representative slice is selected from the filtered slices (S202) either automatically based on slice position, manually by a clinician, semi-automatically by offering choices of representative slices via the GUI 50, or the like. The intensity distribution of the representative slice is normalized to adjust the range of pixel intensities (S204). One approach for normalizing the representative slice is to update each pixel according to the inverse tangent of the corresponding pixel intensity over the overall maximum pixel intensity of the representative slice:

$$I(i, j) = a\tan\left(\frac{I(i, j)}{I_{max}}\right) \times 100$$

where I(i,j) is the pixel intensity at location (i,j), $I_{max}$ is the overall maximum pixel intensity of the representative slice, and 100 is a constant factor.

Figure 3:
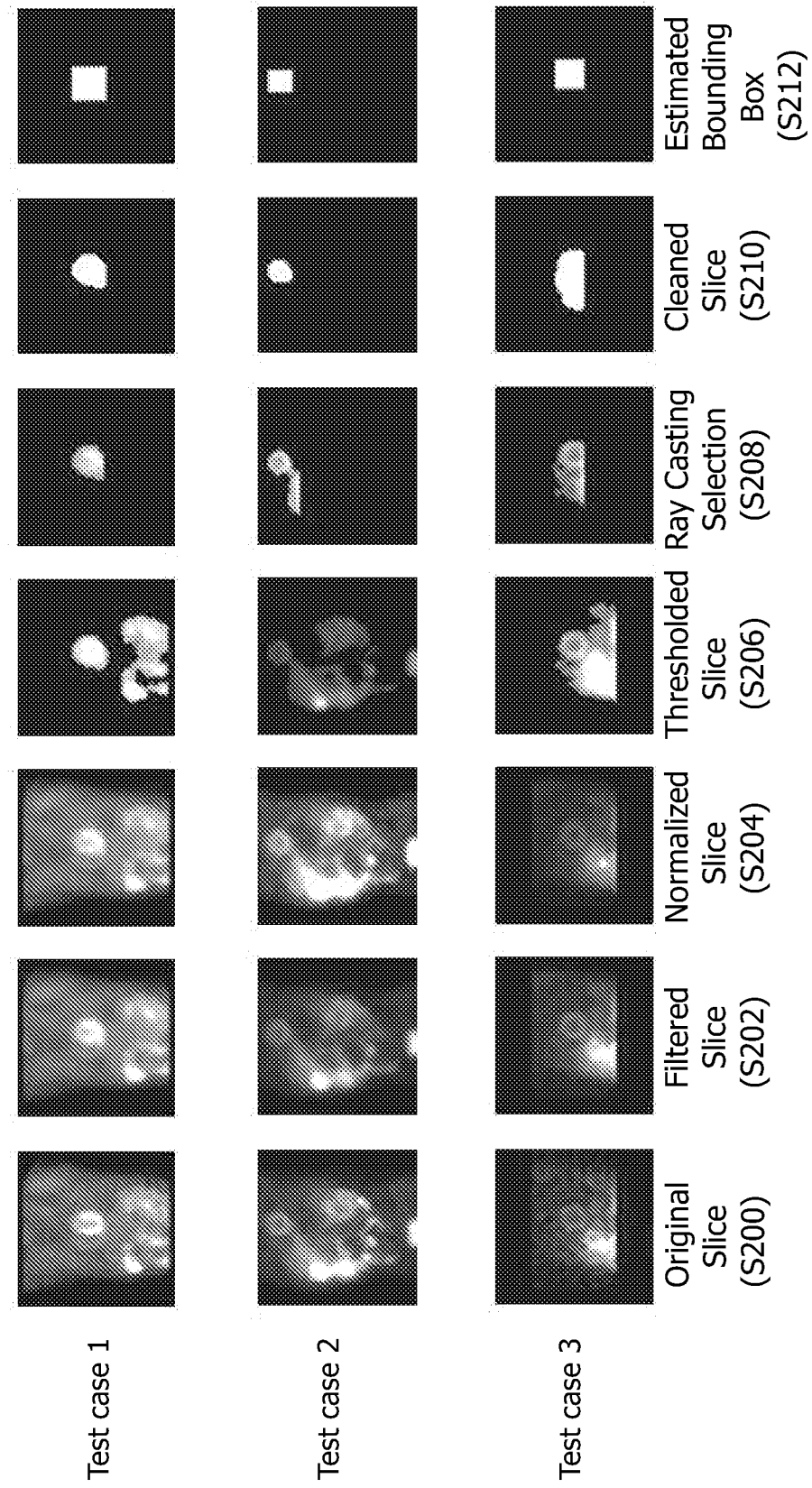
FIG. 3 illustrates screen shots of the projection image at various steps of the method of FIG. 2 for three test cases.
Figure 4A:
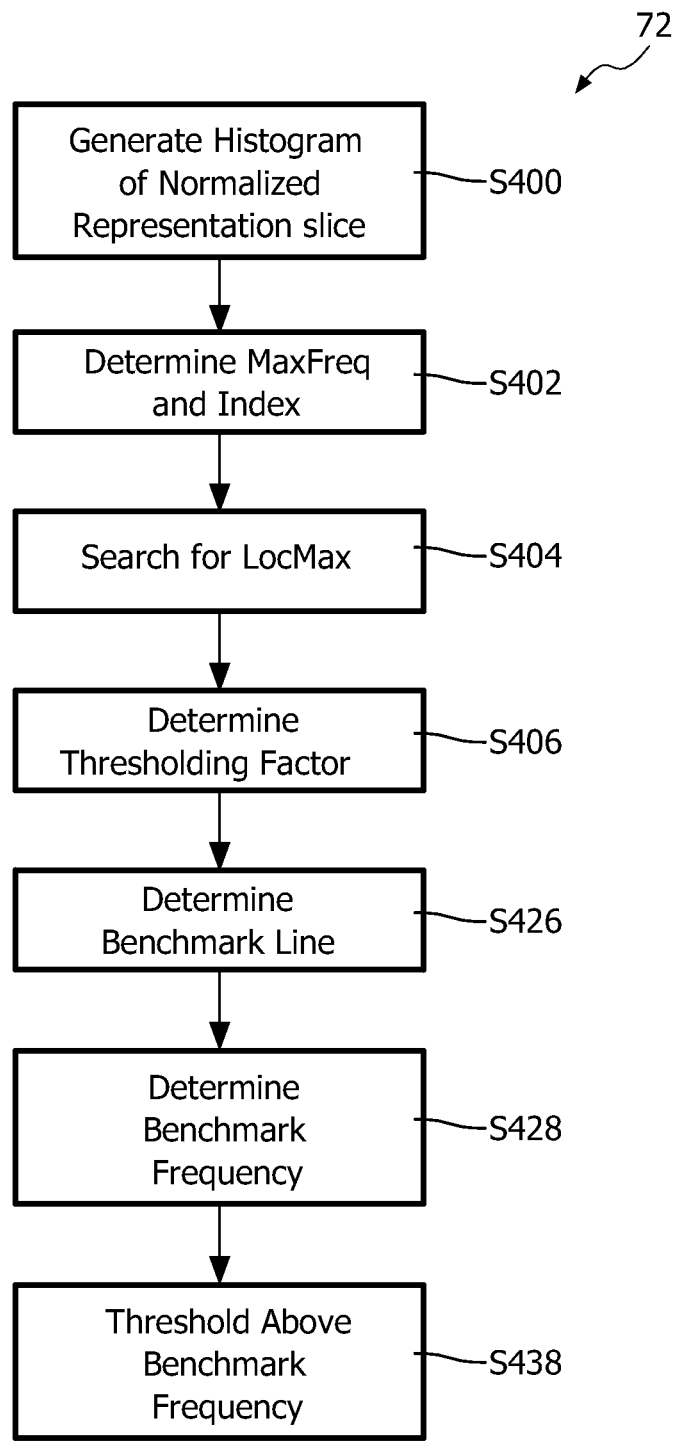
FIG. 4A is a flow diagram representing a method for histogram based thresholding.
Figure 4B:
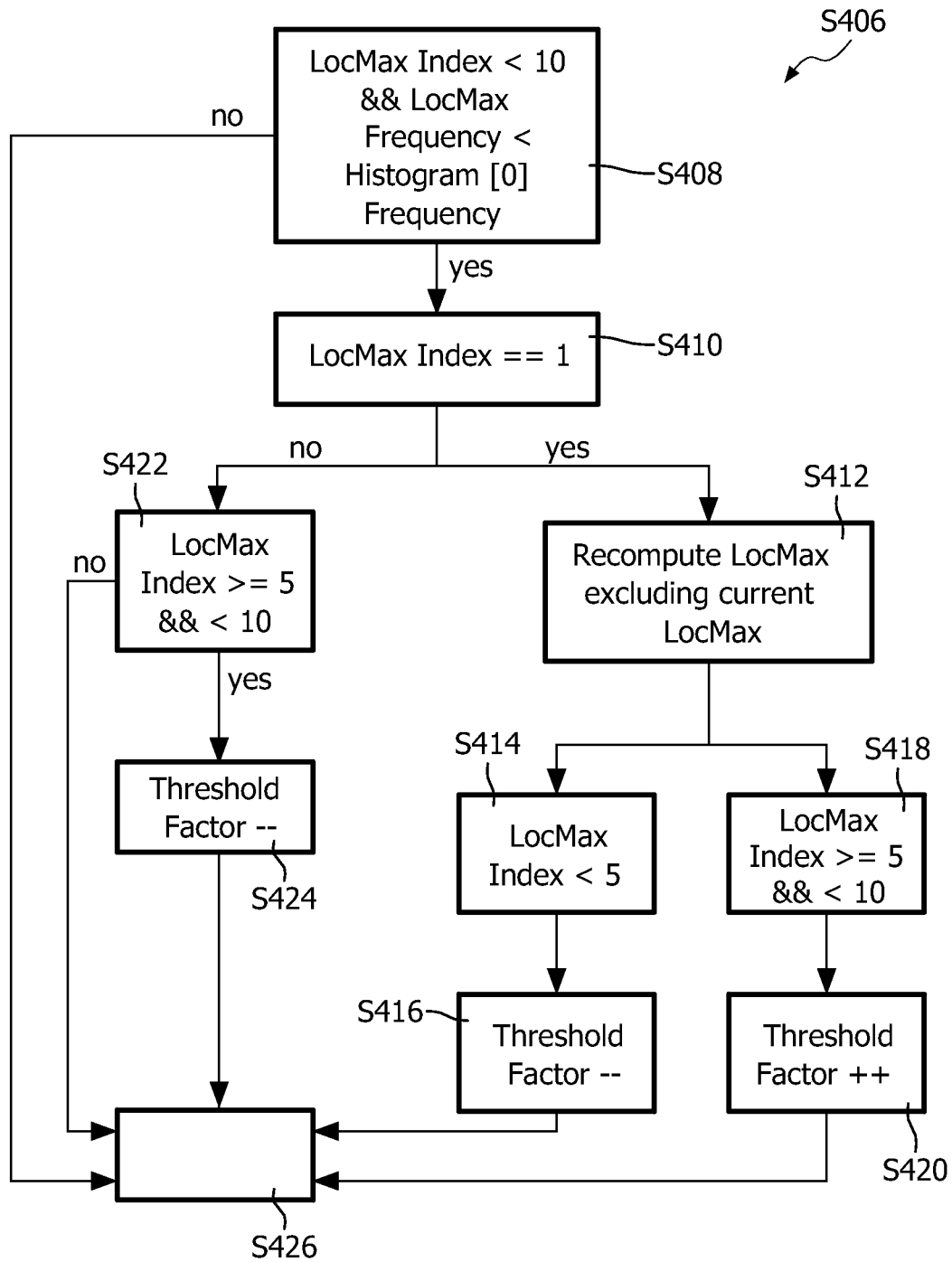
FIG. 4B is a flow diagram representing a method for determining a thresholding factor for use in the histogram based thresholding method.
Figure 4C:
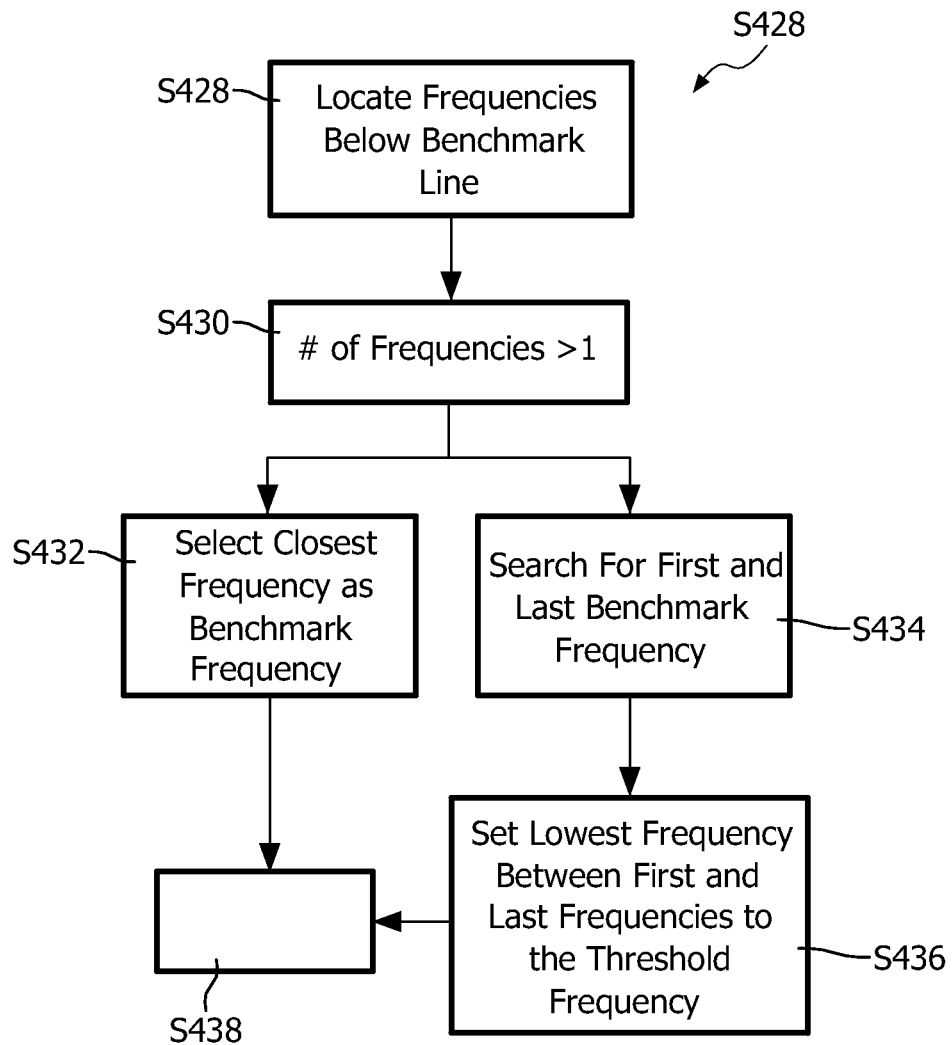
FIG. 4C is a flow diagram representing a method for determining a benchmark frequency for use in the histogram based thresholding method.

The intensity normalized representative slice is thresholded using a histogram profile (S206) in order to retain the high uptake regions, e.g. cardiac region, liver region, abdominal structures, etc., and suppress background noise. To segregate the cardiac region from the other high uptake regions, ray casting is performed to the thresholded slice to localized the cardiac region (S208). After the cardiac region is localized, unnecessary masses surrounding the cardiac region such as portions of the right ventricle, overlapping liver and chest regions, or the like are cleaned or removed using image processing based techniques and/or heuristics (S210). Once the localized cardiac region is cleaned, a bounding box surrounding the localized cardiac region is estimated (S212) and the extents of the myocardium can be determined from the position and dimensions of the bounding box. FIG. 3, illustrates the selected representative slice at various steps of the method 70 on three test cases.

With reference to FIGS. 4A-C and FIG. 5, in order to retain the high uptake regions in the representative slice and to suppress the background noise, the histogram based thresholding of the representative slice is performed. Since a thresholding algorithm 72 should not remove the cardiac region, an iterative adaptive histogram based thresholding algorithm is introduced. Factors such as a local maxima of the histogram, the index at which local maxima occurs, valleys in the histogram, or the like are studied before deciding a thresholding factor. Once the thresholding factor is determined, the normalized representative slice is then determined based on a ratio of the local maxima and the thresholding factor. Clinical studies showed that the thresholding factor is estimated to lie within the range of 2.5 to 5. Therefore, the initial thresholding factor is set to three and the thresholding algorithm 72 iteratively updates the thresholding factor according to the histogram factors.

Figure 5:
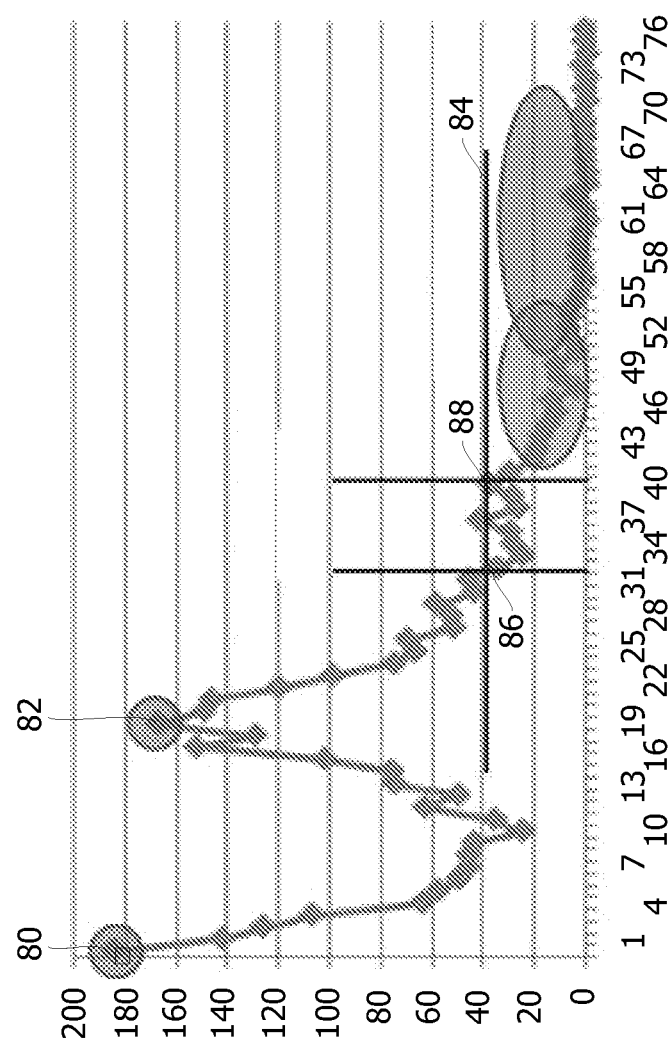
FIG. 5 is a histogram for use in the histogram based thresholding method.

A histogram of the normalized representative slice is generated (S400). A histogram is a graphical display of tabulated frequencies of pixel intensity in the normalized representative slice, as shown in FIG. 5. A maximum frequency 80 (Max-Freq) and its corresponding index is determined from the histogram (S402). Note that the frequency corresponding to histogram index zero is not considered in the thresholding algorithm 72 because they pertain to the background, i.e. pixels with intensity zero. After the MaxFreq is determined, a local maxima (LocMax) 82 within the histogram and its corresponding index is searched for based on a certain preselected conditions (S404).

The conditions can be set by the clinician by inputting the preselected constraints into the GUI using the input device 50 of the console 46. The conditions may include frequency and/or index constraints. For example, the conditions may specify that the difference of the frequency of MaxFreq and LocMax shall be at most 20% of the frequency of MaxFreq. In other words, the frequency of LocMax should be within 20% of the frequency of MaxFreq. Another condition may include that the index of LocMax shall be greater than or equal to eight more than the index of MaxFreq. It should be appreciated the search for the LocMax should not be limited to the example conditions and that other conditions and quantities of conditions are also contemplated.

Once LocMax is determined, the initially set thresholding factor is iteratively determined based on the frequency and index of LocMax (S406). If the index of LocMax is less than 10 and frequency of LocMax is less than the frequency of the background (i.e. histrogram[0] or pixels with zero intensity) then the thresholding factor is updated (S408). If both of these conditions are met, then the algorithm 72 determines if noise is dominating by checking if the index of LocMax is equal to one (S410). If LocMax is equal to one, then a new LocMax is searched for excluding the current LocMax (S412), i.e. excluding index one and the associated frequencies from the search. If the new LocMax index is less than five (S414), then the thresholding factor is reduced by one (S416) and the algorithm continues. If the new LocMax index is greater than or equal to five and less than ten (S418), then the thresholding factor is increased by one (S420) and the algorithm continues. If LocMax is not equal to one, then check if the LocMax index is greater than or equal to five and less than ten (S422). If so, then the thresholding factor is reduced by one and the algorithm continues (S424).

If the test of step S408 fails then the algorithm continues to determine a benchmark line 84 according to a ratio of the LocMax frequency to the determined threshold factor (S426):

$$y = \frac{LocMax \text{ Frequency}}{\text{Threshold Factor}}$$

Benchmark frequencies are then determined (S428) to be frequencies that are below the benchmark link 84. The benchmark frequencies establish a range for thresholding above a one of the determined benchmark frequencies, i.e. indices above and/or including a thresholding frequency are preserved after thresholding. First, all the frequencies below the benchmark line are located and labeled benchmark frequencies. If the number of number of frequencies is less than one (i.e. there are no frequency below the benchmark line) (S430), than the frequency closest to the benchmark line is searched for and selected as the benchmark frequency (S432).

If the number of benchmark frequencies is greater than or equal to one (S430), then a first and last benchmark frequency are searched for (S434). The first benchmark frequency 86 is the first histogram frequency just below the benchmark line. The last benchmark frequency 88 is the histogram frequency between the first benchmark frequency and the benchmark line and with an index between three to fifty of the first benchmark point index. The threshold frequency is the lowest frequency between the first and last benchmark frequency (S436), i.e. it is the valley. After the benchmark frequency is determined (S428), the normalized representative slice is thresholded above the determined benchmark frequency (S438).

Figure 6A:
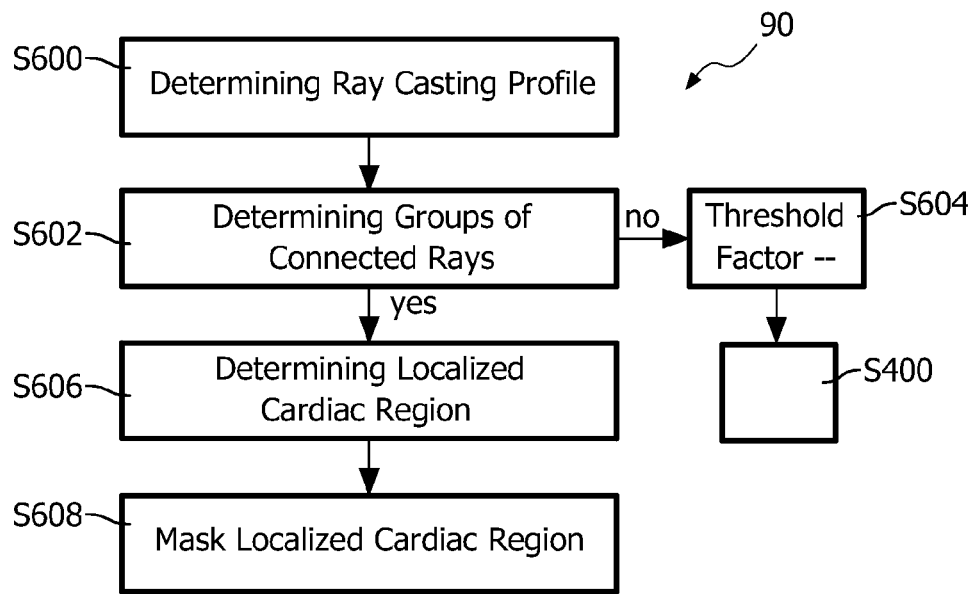
FIG. 6A is a flow diagram representing a method for ray casting based localization of a cardiac region.
Figure 6B:
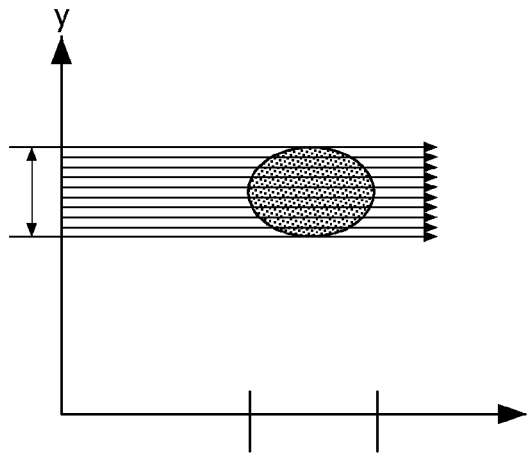
FIG. 6B is a chart depicting horizontal rays casted in the y-direction.
Figure 6D:
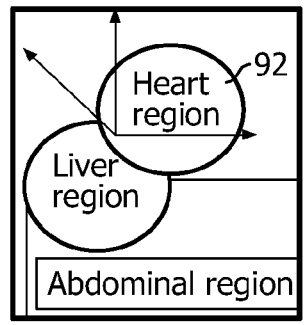
FIG. 6D is an illustration of anatomical heuristics for use in ray casting based localization.
Figure 6C:
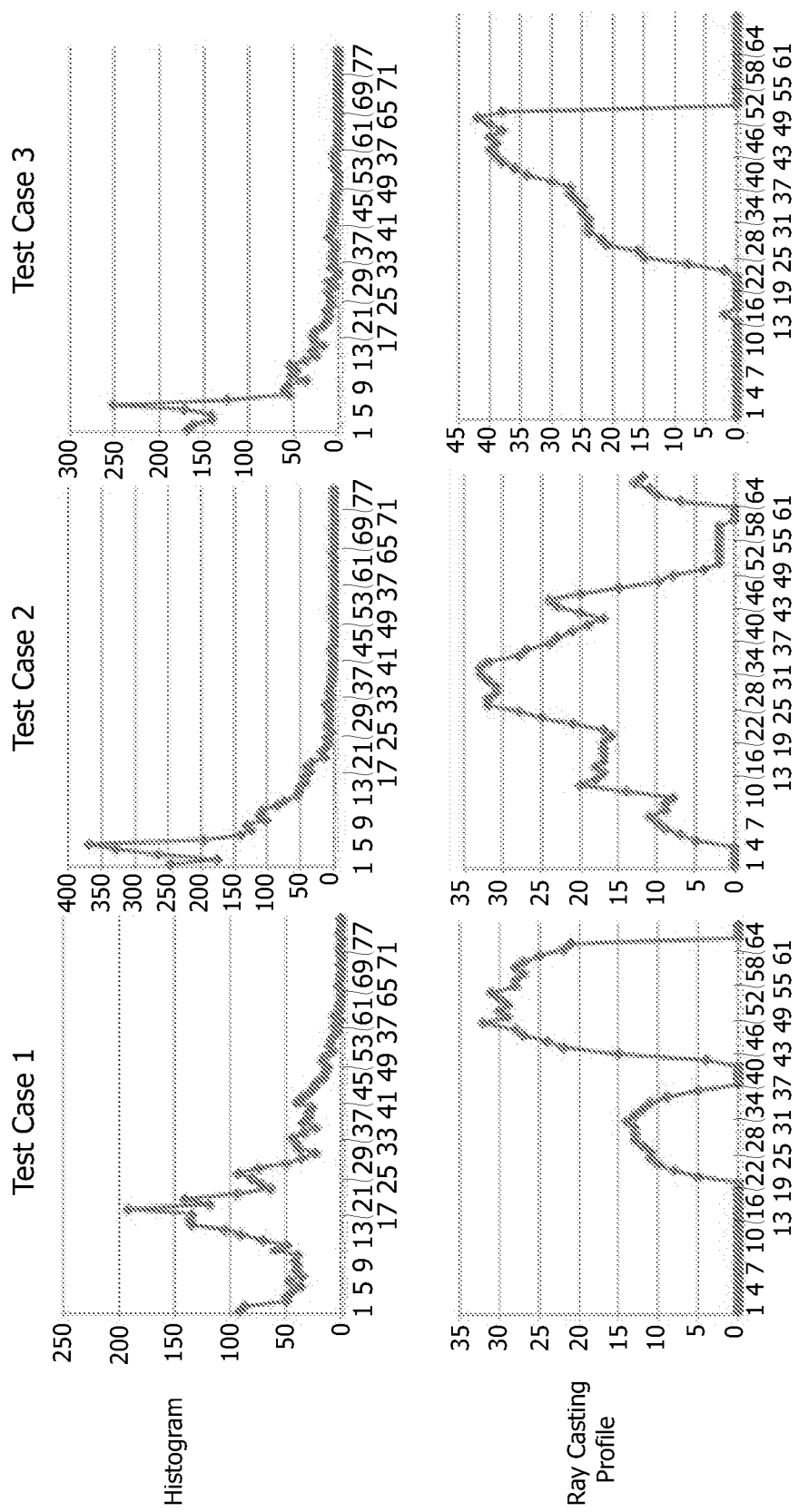
FIG. 6C illustrates the histogram and associated ray casting profile for the three test cases.

Returning to FIG. 2 and continuing with reference to FIGS. 6A-C, the localized cardiac region is determined from the thresholded representative sliced (S208) according to a ray casting algorithm 90. To determine localized cardiac region, a horizontal ray casting profile is generated (S600) as shown in FIG. 6B. The rays casted horizontally starting with first row and progressing in the y-direction of the thresholded slice. Examples of the ray casting profile are illustrated in FIG. 6C for the three test cases. The first row is the histogram of the normalized representative slice and the second row is the corresponding ray casting profiles. The y-axis of the histograms represents the frequency and x-axis represents the pixel intensity or index. In the ray casting profiles, the y-axis represents the count of non-zero pixels and x-axis represents the rays that are casted, e.g. 64 rays are casted.

Returning to FIG. 6A, from the ray casting profile, groups of rays with non-zero counts are determined to be connected based on a connectivity criteria. As with the LocMax conditions, a clinician can set the connectivity criteria by inputting the constraints into the GUI of the console 46 using the input device 50. For example, the connectivity criteria may be based on certain anatomical assumptions such as the dimensions of the myocardium and/or the position of the myocardium. The clinician can enter the subject's age, height, weight, chest size, past history, or the like into a database to retrieve average dimensions and positions as a basis for the assumptions. In regards to SPECT imaging, a slice with approximate dimensions of 410 mm×410 mm with a 64×64 pixel resolution, it can be assumed that the myocardium has at least a vertical dimensions of 38.4 mm or 6 rays or 6 pixels and a horizontal dimension of at least 44.8 mm or 7 columns or 7 pixels for 25% of the horizontal rays. If the connectivity criteria fails to short list the myocardium, e.g. a group of connected rays do not meet a minimum dimension criteria, then thresholding factor is reduced by one (S604) and the histogram based thresholding is repeated with the updated thresholding factor.

If the connectivity criteria are met and a region is short listed as the myocardium (S602), then a localized cardiac region is determined (S604) and further processed to determine the ROI and corresponding reconstruction extents. The region beginning with the first (anterior) non-zero ray short-listed as the myocardium from the previous step extending 76.8 mm, or 12 pixels for the 64×64 SPECT slice, is determined as the localized cardiac region (S606). The localized cardiac region is preserved by masking out noise and the high intensity abdominal region and liver then further processing the masked region. FIG. 6D illustrates an example of the heuristics used to determine the connectivity criteria to short list the myocardium and to determine the localized cardiac region 92.

Figure 7A:
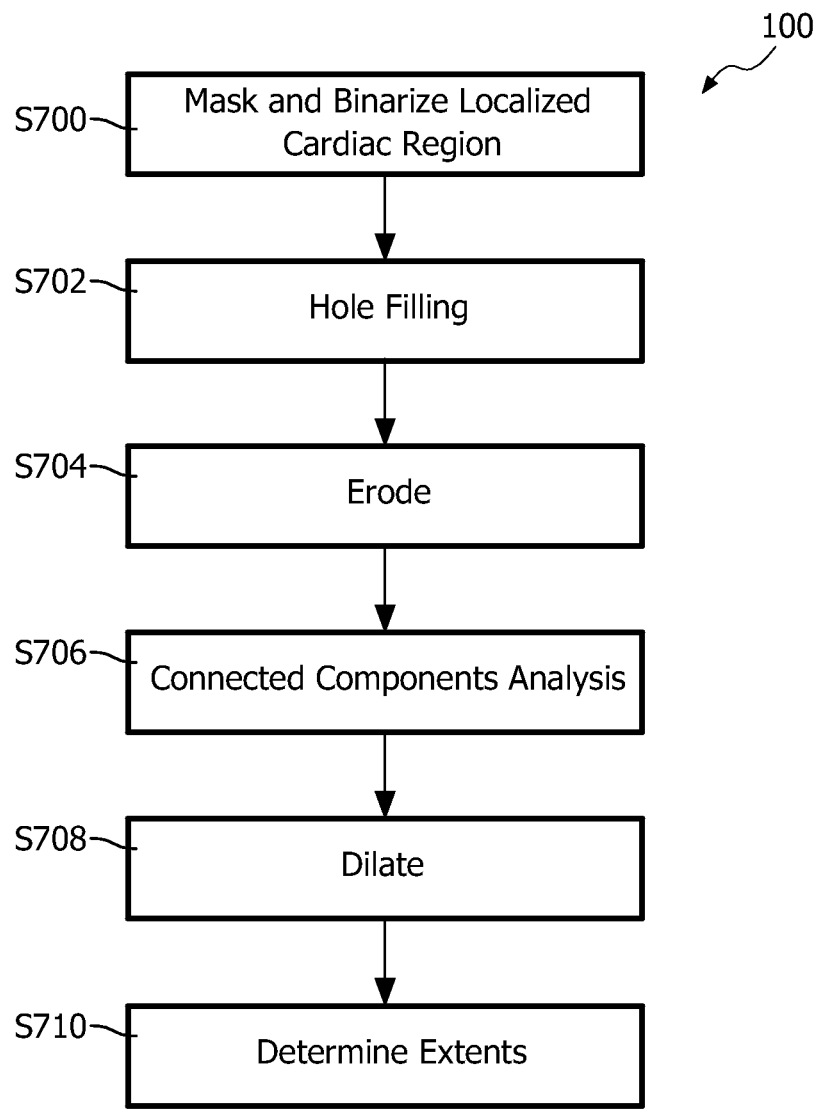
FIG. 7A is a flow diagram representing a method for image processing based cleaning techniques of a localized cardiac region.
Figure 7B:
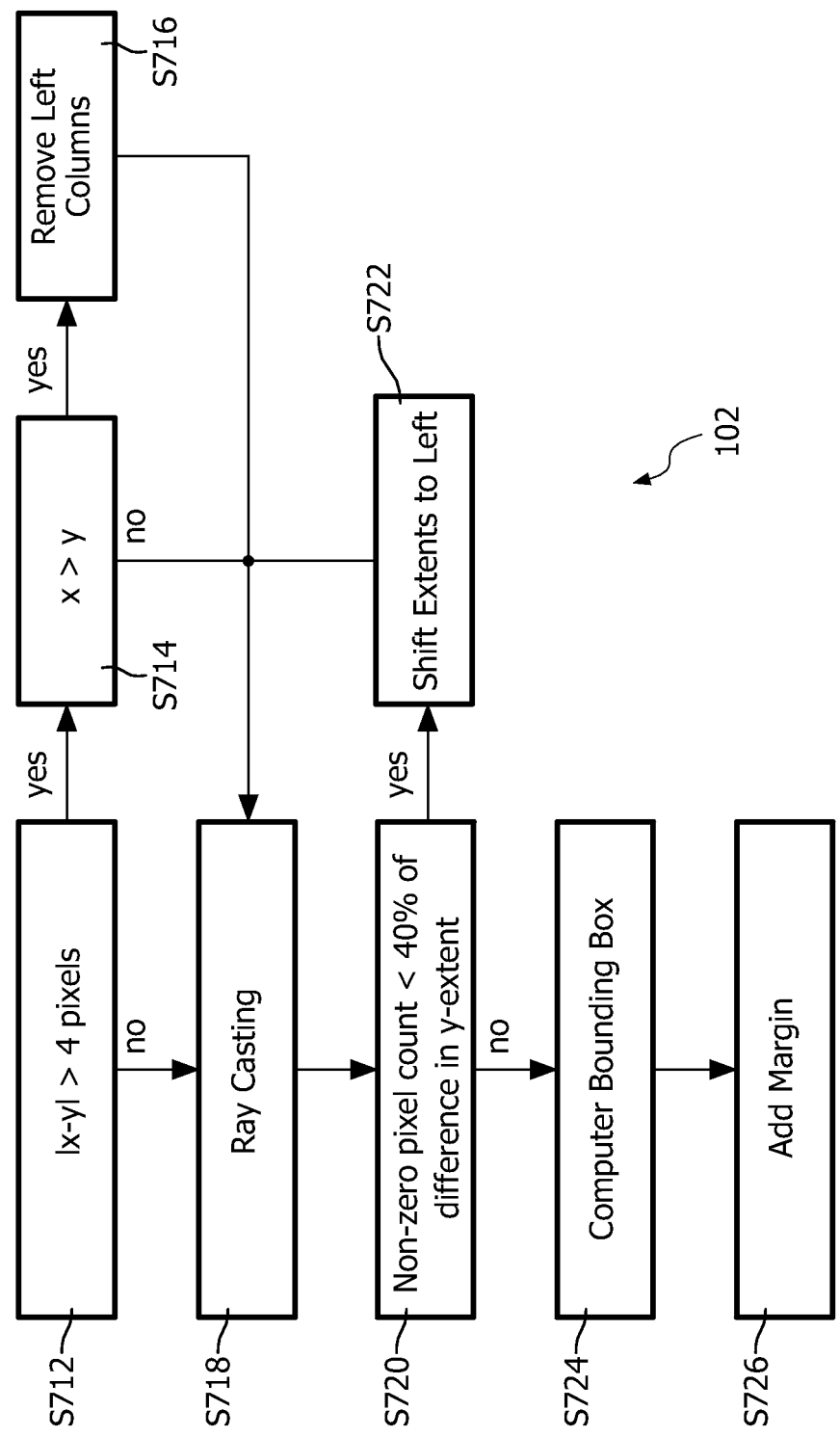
FIG. 7B is a flow diagram representing a method for heuristics based cleaning techniques of a localized cardiac region.

With reference to FIGS. 7A and 7B, after initial segregation and ray casting operation (i.e. in the vertical direction), the myocardium is cleaned in horizontal direction from unnecessary mass such as portions of right ventricle, overlapping liver, and other chest regions surrounding heart. Image processing techniques 100 are employed and heuristics based cleaning algorithm 102 is employed for the same. The masked slice determined after ray casting (S206) is binarized (S700).

In some cases, holes may appear in the binarized image representation because of the low intensity pixels within the myocardium boundary. A hole filling operation (S702) is performed to ensure that regions of the myocardium are not removed in a subsequent erosion operation (S704). Connected components analysis (S706) is performed and components with at least 10 pixels are selected and the selected components are dilated (S708). Once the dilated binary mask is obtained, extents are computed in the x and y-directions (S710).

The heuristics based cleaning algorithm 102 cleans the remaining mass. If extents in x and y-directions differ by more than 4 pixels (S712) and the mass in the x-direction is greater than the y-direction (S714), then the mass in the x-direction is removed, i.e. columns are iteratively deleted, from the dilated binary mask from left direction until the difference in extents become same as the difference in Y direction (S716). If extents in X and Y direction is less than 4 pixels, next step is executed.

After estimating the appropriate extents, rays are casted in the y-direction along the x-axis and if the number of non-zero pixels along each ray are counted starting from right (S718). For each non-zero ray, if the number of non-zero pixels is less than 40% of the extents in y-direction (S720), then the extents in the x-direction are shifted or adjusted to the left (S722). The shifting is repeated until the number of non-zero pixels of the current ray is greater than or equal to that of the extents in y-direction. Once this process stops, a bounding box is estimated of the remaining mass (S724) and a margin, e.g. ±4 pixels, in both the x and y-direction of bounding box are added (S726) to give the reconstruction limits The final reconstruction limits can be masked over the functional imaging representation, projection image representation, volumetric image representation, or the like for viewing on the display unit 48 for verification by the clinician.

Figure 8A:
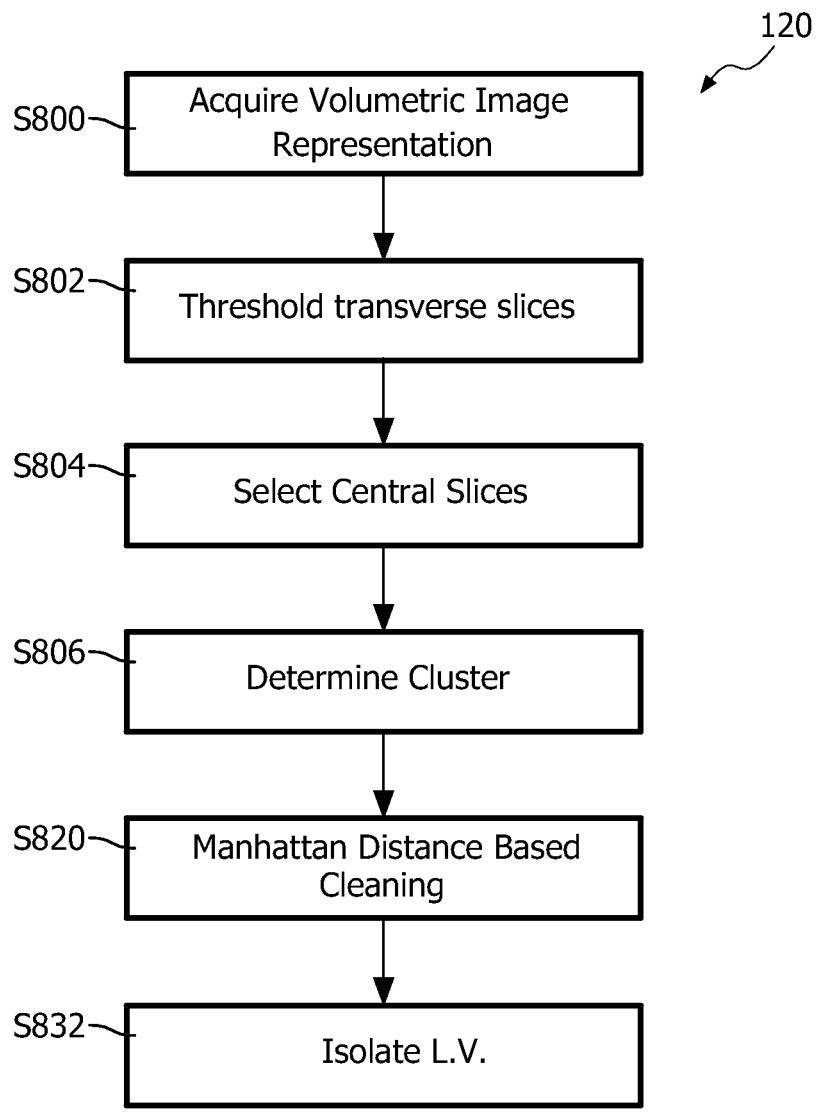
FIG. 8A is a flow diagram representing a method for determining a myocardial region of interest from volumetric images.

With reference to FIG. 8A, in another embodiment, the ROI processor 60 is configured to perform a method 120 for determining an ROI that at most includes the left ventricle and reorients of the left ventricle (L.V.). For parameter quantification and estimation, the L.V. is reoriented. Typically, the entire volumetric image representation is reoriented in order to orient the short axis, horizontal long axis, and vertical long axis of the left ventricle. Knowledge of this LV orientation enables the appropriate slicing of volumetric tomographic data for accurate and repeatable assessment of diagnostic parameters such as myocardial blood flow, regional myocardial blood flow, flow reserve, ejection fraction, and the like. Misalignments between studies, such as stress and rest tests, can result in misdiagnosis. To improve the accuracy and repeatability of L.V. reorientation, the method 120 calls for the identification of a ROI which includes at most the left ventricle and reorienting just the ROI instead of the entire volume.

The ROI processor 60 receives the volumetric image representation stored on the projection image memory 40 (S800). The transverse slices that make up the volumetric image representation are individually thresholded (S802) in order to retain the myocardial boundary and suppress background noise and intensities emanating from the liver and abdominal regions that may in turn interfere with parameter estimation and quantification. A maximum intensity for each transverse slice is determined, then the slice is thresholded such that the pixels with intensities above a ratio of the determined maximum intensity over a preselected thresholding factor, e.g. 2, are preserved. Once the transverse slices have been thresholded, a central set of slices which correspond to the myocardium are selected (S804). In the example of SPECT imaging, the central slices are expected to be 30-40% of the transverse volume which may include approximately seven slices. The central slices can be determined automatically based on slice position within the transverse volume, manually by a clinician, or a combination thereof such as by providing a selection of central slices for verification of a suitable set via the GUI.

Figure 8B:
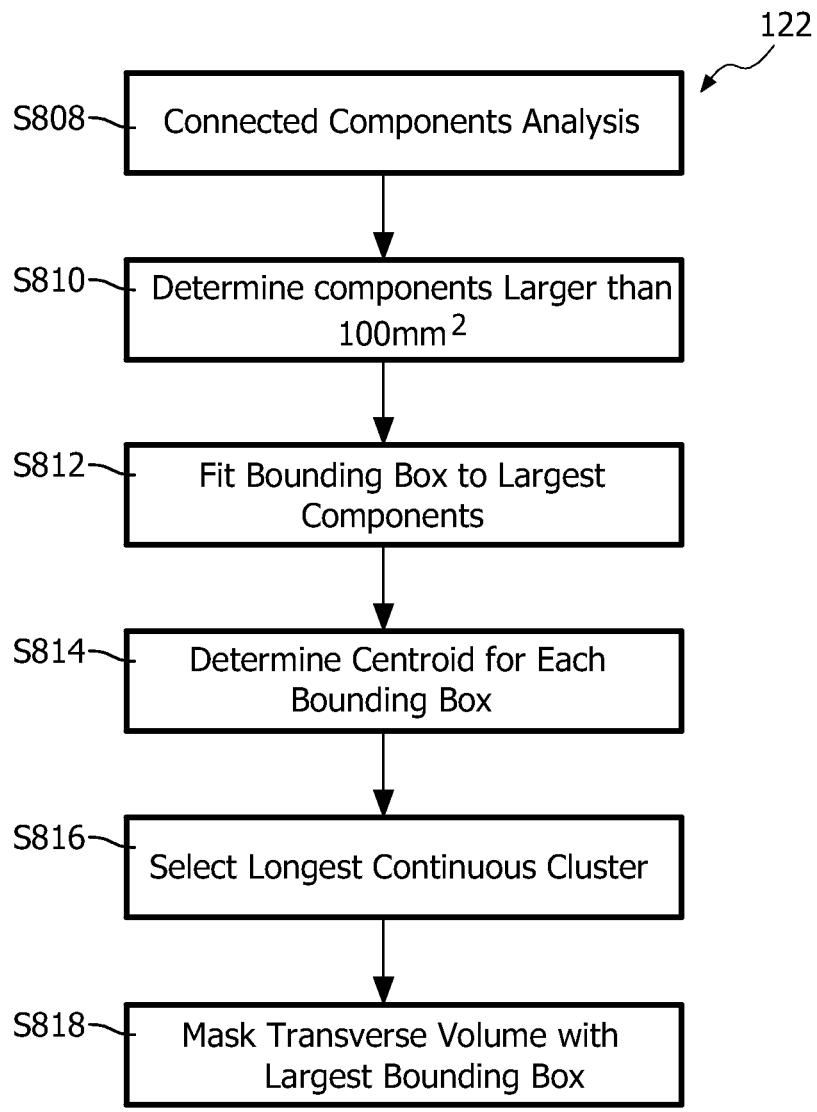
FIG. 8B is a flow diagram representing a method for clustering to segregate a left ventricle.

Once the set of centrally located slices corresponding to the myocardium is selected, clustering is performed on each of the selected slices (S806) to segregate the L.V. from the liver and abdominal regions. Continuing with reference to FIG. 8B, the clustering algorithm 122 first determines the largest component within each of the selected slices with connected components analysis (S808). Components with areas larger than 100 mm$^2$ (S810), or approximately 15-16 pixels in a 64×64 slice, are fitted with a bounding box (S812). The centroid for each bounding box is determined (S814) then adjacent centroids are analyzed in the transverse direction. The longest continuous cluster of bounding boxes with aligned centroids is selected and the largest bounding box within the selected cluster is used to mask the entire volumetric image representation (S818) which defines the initial ROI. The degree of alignment is determined by the distance between centroids in adjacent slices. For example, adjacent centroids within 4 pixels, or 25.6 mm, in either the x or y-direction are considered continuous. FIG. 8D illustrates the selected central slices (first row) after the thresholding (second row) and cluster selection (dotted line in third row).

Figure 8C:
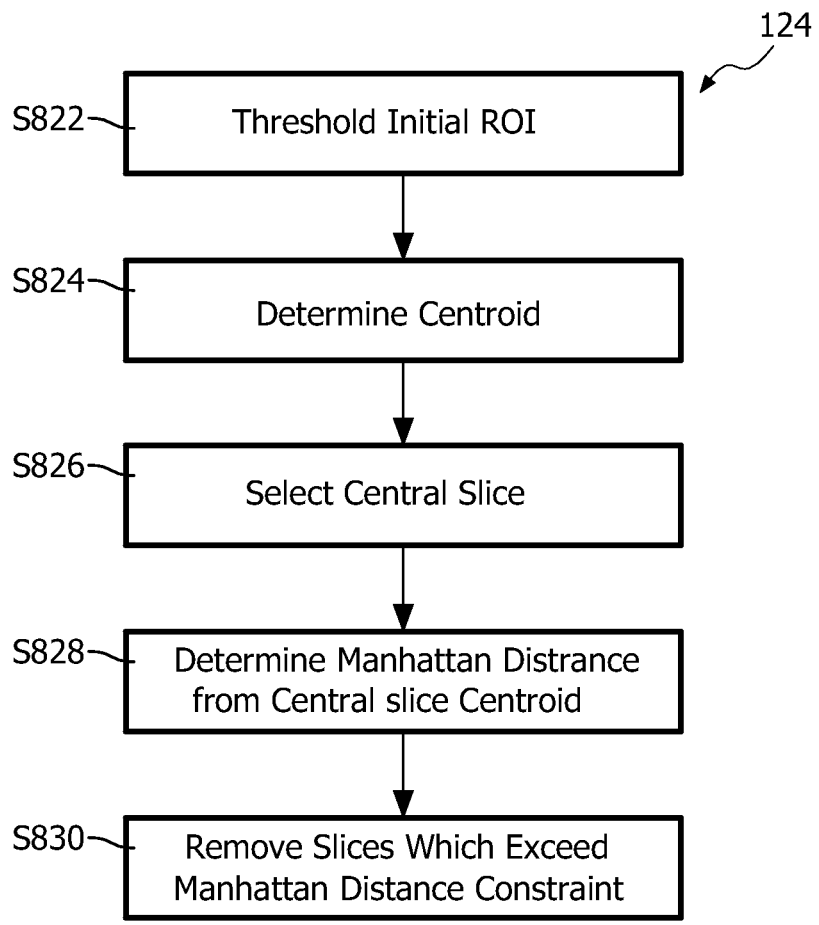
FIG. 8C is a flow diagram representing a method for Manhattan based cleaning of an initial region of interest.
Figure 8D:
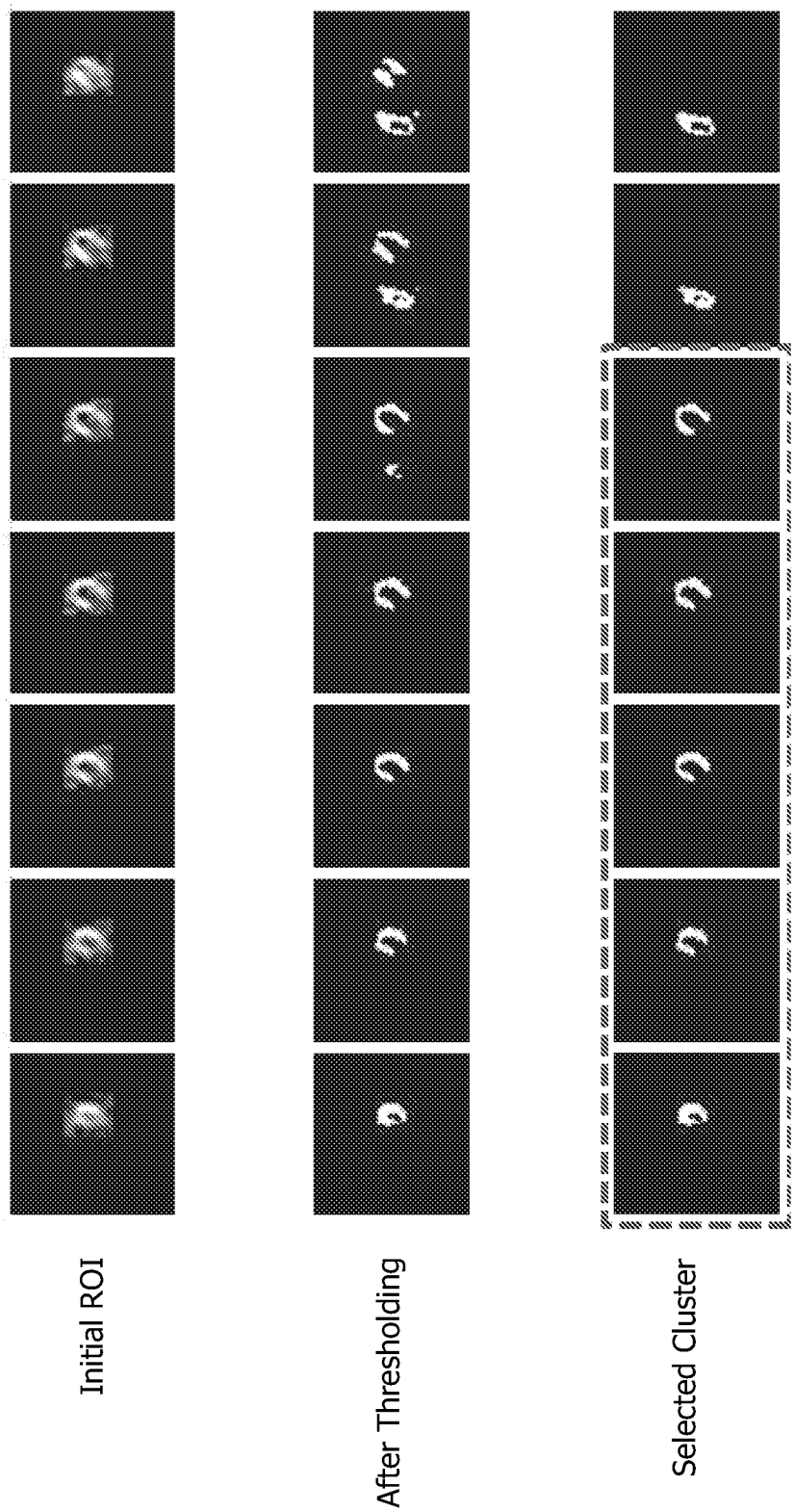
FIG. 8D illustrates screen shots of the initial region of interest and selected cluster.
Figure 8E:
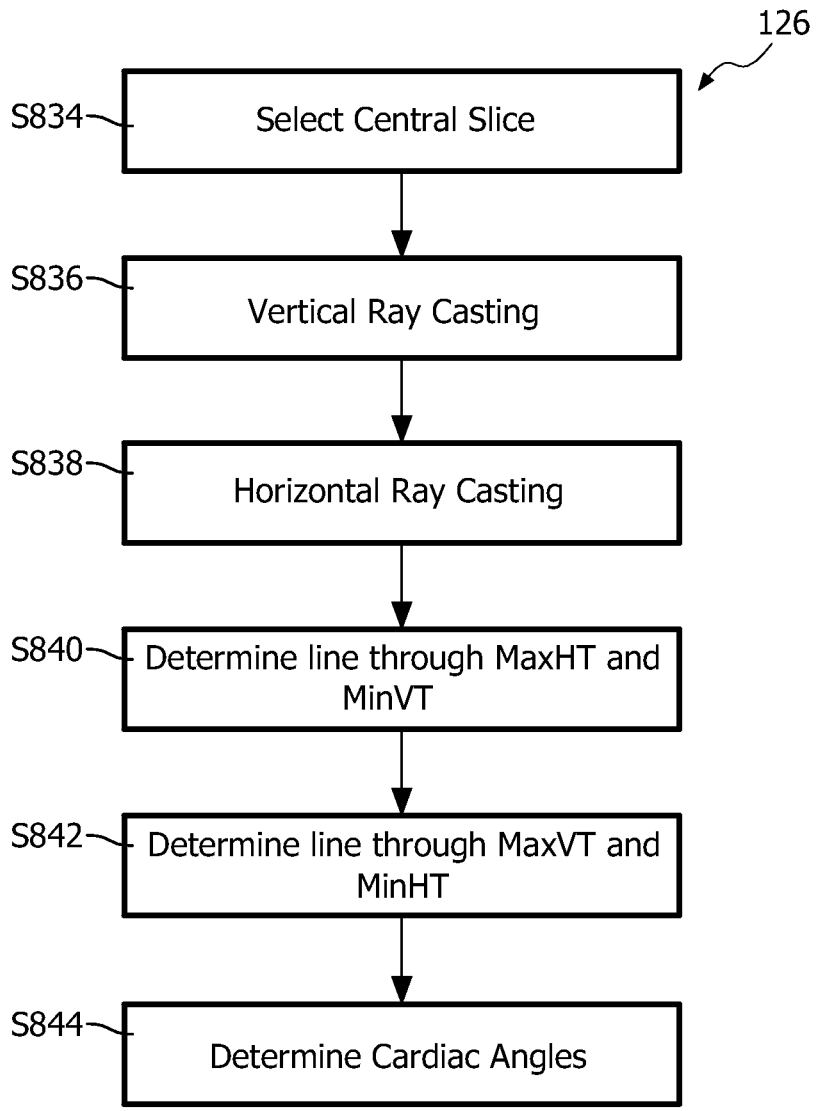
FIG. 8E is a flow diagram representing a method for isolating the left ventricle and determining associated cardiac angles.

With returning reference to FIG. 8A and continuing with FIG. 8C, the masked ROI determined from the clustering algorithm 122 covers all slices in the transverse direction. This initial ROI may have certain abdominal or liver portions in it which are cleaned in the transverse direction according to a Manhattan distance (S820). A Manhattan distance algorithm 124 ensures that myocardium mass present in each slice is in coordination, and any mismatch is appropriately adjusted.

The initial ROI is thresholded (S822) slice-wise using the maximum intensity of the initial ROI over a preselected thresholding factor. A centroid of the remaining mass after thresholding is determined (S824) for each slice of the initial ROI. A Manhattan distance is determined (S828) for each slice centroid from a centroid of a selected center slice (S826). Based on a preselected constraint on each determined Manhattan distance, e.g. 20 mm slices, the slices of the thresholded ROI which are beyond the preselected Manhattan distance constraint from selected central slice are removed from the ROI (S830). The algorithm 124 traverses towards the end and towards the start of the transverse volume from the central slice, and determines the start and end of ROI according to the Manhattan distance.

After Manhattan distance based cleaning, the cleaned ROI may have certain overlapping regions of liver and abdominal areas with that of myocardium. The L.V. is isolated (S832) from these regions which may interfere with determining cardiac angles. For this purpose lines parallel to a septum of the L.V. are estimated on the myocardial wall in the central slice. The ROI mass between these determined lines are preserved for L.V. reorientation.

Figure 8F:
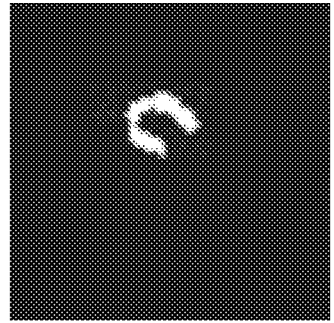
FIGS. 8F-8I illustrate screenshots of the method of FIG. 8E.
Figure 8G:
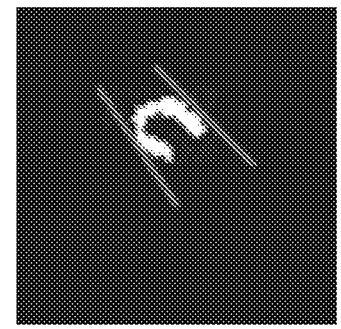
Figure 8H:
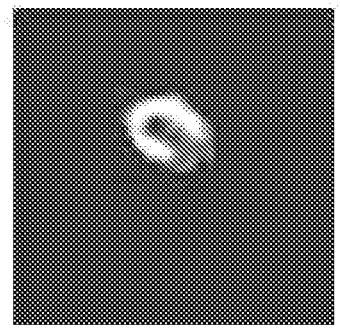
Figure 8I:
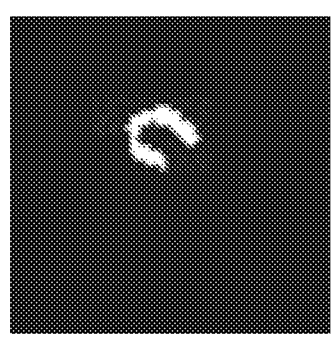

With reference to FIGS. 8E-8H, the L.V. isolation algorithm 126 is performed on a selected central slice. Ray casting in the vertical and horizontal direction is used to determine a maximum vertical tangent (MaxVT), minimum vertical tangent (MinVT), maximum horizontal tangent (MaxHT), and minimum horizontal tangent (MinHT) as illustrated in FIG. 8F. The first ray with a non-zero count in either the positive and negative y-direction (FIG. 8G) are used determine the maximum and minimum vertical tangent points (S836). The first ray with a non-zero count in either the positive and negative x-direction (FIG. 8H) are used determine the maximum and minimum horizontal tangent points (S838). Lines connecting the MaxHT to the MinVT and the MaxVT ro the MinHT (S840, S842) define the cardiac angles as shown in FIG. 8I. The angles are determined from the tangent of the slope of each line where the slope is determined by y=mx+b (S844).

Figure 8J:
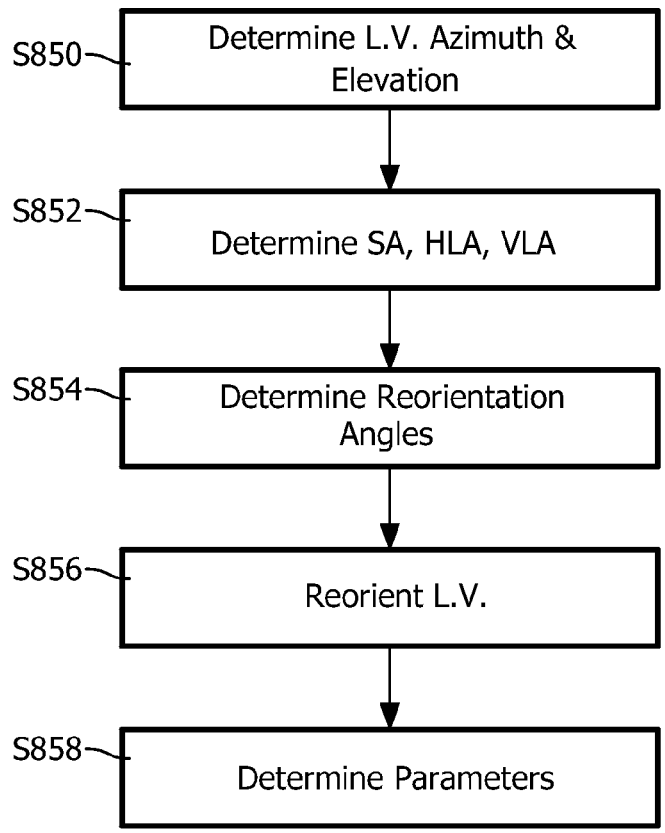
FIG. 8J is a flow diagram representing a method for reorienting the left ventricle.
Figure 8K:
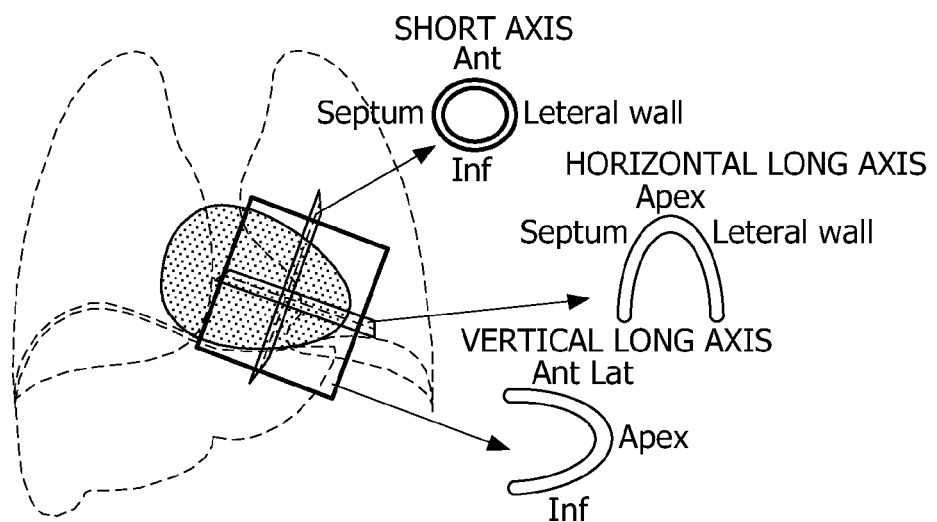
FIG. 8K illustrates dimensions of the left ventricle determined for reorientation of the left ventricle.

With reference to FIGS. 8J and 8K, the mass between these lines are isolated and the cardiac lines are used to determined the azimuth and elevation angle (S850) of the L.V. from which the short axis (SA), horizontal long axis (HLA), vertical long axis (VLA) are determined (S852). With the SA, HLA, and VLA the ROI processor 60 determines the reorientation angles (S854) and reorients the L.V. (S856).

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiment, the invention is now claimed to be:

1. A method for cardiac imaging, comprising:
  acquiring functional imaging data of a subject, the functional imaging data including at least a myocardium;
  determining a region of interest (ROI) encompassing at most the myocardium from the acquired functional imaging data, determining the ROI including:
    generating projection image representations from the functional image data,
    thresholding the projection image representation based on a histogram of a selected representative slice,
    determining a localized cardiac region within the thresholded data according to at least one of a horizontal ray casting profile and anatomical heuristics, and
    determining extents of the localized cardiac region according to image based and heuristics based cleaning techniques; and
  estimating diagnostic parameters of the myocardium based on the determined ROI.

2. The method according to claim 1, wherein the estimated diagnostic parameters include at least one of myocardial blood flow, regional myocardial blood flow, flow reserve, and ejection fraction.

3. The method according to claim 1, wherein thresholding the acquired functional data includes:
  generating a histogram of the selected representative slice;
  determining a maximum frequency and its index from the histogram;
  searching for a local maximum frequency and its index based on preselected conditions on the basis of the index of the maximum frequency; and
  iteratively determining a thresholding factor based on at least one of an index and frequency of the local maximum frequency.

4. The method according to claim 3, wherein thresholding the projection image representation further includes:
  determining a benchmark line from a ratio of the local maximum frequency to the determined thresholding factor;
  locating a first benchmark frequency and its index on the histogram, the benchmark frequency being a first frequency below the benchmark line;

locating a last benchmark frequency and its index, the last benchmark frequency having a frequency between the first benchmark frequency and the benchmark line and an index between three to fifty of the first benchmark point index;

locating the thresholding frequency and its index, the threshold frequency being lowest frequency between the first and last benchmark frequencies; and thresholding the projection image representation such that the frequencies with indices greater than or equal to the second benchmark index are preserved.

5. The method according to claim 4, wherein determining a localized cardiac region within the thresholded data include:

generating the ray casting profile of the thresholded projection image representation from horizontally casted rays;

determining ray which are connected according to connectivity criteria; and determining the localized cardiac region according to anatomical heuristics to the connected rays.

6. The method according to claim 5, wherein the anatomical heuristics defining a localized cardiac region according to approximate cardiac dimensions and anatomical position based on non-zero pixel counts of casted rays.

7. The method according to claim 5, wherein in response to the determined localized cardiac region failing, updating the thresholding factor and thresholding the projection image representation according to an updated benchmark line and/or frequencies.

8. The method according to claim 5, wherein determining the extents of the localized cardiac region includes:

masking the determined localized cardiac region;

cleaning the masked localized cardiac region using image based cleaning techniques;

determining extents of cleaned localized cardiac region;

adjusting extents of cleaned localized cardiac region according to vertical ray casting based heuristics; and estimating a bounding box for the adjusted extents.

9. The method according to claim 1, further including:

reconstructing the functional imaging data which correspond to the determined extents of the localized cardiac region.

10. A method for cardiac imaging, comprising:

acquiring functional imaging data of a subject, the functional imaging data including at least a myocardium;

determining a region of interest (ROI) encompassing at most the myocardium from the acquired functional imaging data, determining the ROI including:

reconstructing the function imaging data into a volume image representation;

thresholding transverse slices of the volume image representation according to a maximum pixel intensity of each corresponding slice;

determining a cluster of the thresholded slices which correspond to a left ventricle;

cleaning the determined cluster of slices according to a predetermined Manhattan distance between a left ventricle centroid in a central slice to the left ventricle centroid in the remaining clustered slices; and isolating the left ventricle in the cleaned slices according to cardiac angles of a septum of the myocardium; and estimating diagnostic parameters of the myocardium based on the determined ROI.

11. The method according to claim 10, further including:

determining the azimuth and elevation angle of the isolated left ventricle;

determining a short axis, a vertical long axis, and a horizontal long axis of the left ventricle according to the determined azimuth and elevation angle; and determining reorientation angles of the left ventricle according to the determined short axis, vertical long axis, and horizontal long axis.

12. The method according to claim 10, wherein thresholding the transverse slices includes:

determining a maximum pixel value for each transverse slice; and preserving pixels within each slice with intensities above a ratio of the corresponding maximum pixel value to a preselected thresholding factor.

13. The method according to claim 12, wherein determining a cluster of the thresholded slices includes:

selecting a plurality of centrally located slices which correspond to the myocardium;

determining a largest component within each selected slice according to connected component analysis;

fitting a bounding box around each of the largest components;

determining a longest continuous cluster of bounding boxes with adjacent centroids which differ by less than four pixels; and generating an initial ROI by masking the volume image representation with a largest bounding box within the determined cluster.

14. The method according to claim 13, wherein cleaning the determined cluster of slices includes:

thresholding each slice of the initial ROI according to a ratio of a maximum pixel intensity of each corresponding slice and a preselected thresholding factor;

determining a centroid of each thresholded slice of the initial ROI; and removing slices from the thresholded ROI which exceed a predetermined Manhattan distance from the centroid of a central slice.

15. The method according to claim 10, wherein isolating the left ventricle includes:

selecting a central slice of the cleaned slices;

determining a maximum and a minimum horizontal tangent point and a maximum and a minimum vertical tangent point;

estimating a first cardiac angle of a line between the minimum vertical tangent point and the maximum horizontal tangent point; and estimating a second cardiac angle of a second line between the maximum vertical tangent point and the minimum horizontal tangent.

16. A functional imaging system, comprising:

at least one detector head configured for acquiring functional imaging data;

a controller configured to control the acquisition of the functional image data and/or a position of the detector head;

a region of interest processor configured to determine a region of interest (ROI) encompassing at most a myocardium from the acquired functional imaging data;

a parameterization processor configured to estimate and/or quantifies parameters from the determined ROI; and an electronic data processing component programmed to:

generate projection image representations from the functional image data, threshold the projection image representation based on a histogram of a selected representative slice, determine a localized cardiac region within the thresholded data according to at least one of a horizontal ray casting profile and anatomical heuristics, determine extents of the localized cardiac region according to image based and heuristics based cleaning techniques, and reconstruct the determined image data which corresponds to the determined extents of the localized cardiac region.

17. The functional imaging system according to claim 16, wherein the estimated diagnostic parameters include at least one of myocardial blood flow, regional myocardial blood flow, flow reserve, and ejection fraction.

18. A non-transitory computer readable storage medium containing instructions, when executed by a computer, causes the computer to carry out the method according to claim 1.

19. A non-transitory computer readable storage medium containing instructions, when executed by a computer, causes the computer to carry out the method according to claim 10.

20. The method according to claim 1, wherein in the acquisition step the functional image data is acquired by a nuclear imaging system and the determination and estimation steps are performed with a computer processor and further comprising displaying the localized cardiac region on a display apparatus.

21. The method according to claim 1 wherein acquiring the functional image data includes acquiring nuclear image data from a radioisotope injected into the subject with one of a single photon emission computed tomography system (SPET).

22. An imaging system, comprising:
at least one detector head configured for acquiring functional imaging data;
a controller configured to control the acquisition of the functional image data and/or a position of the detector head;
an electronic data processing component programmed for:
reconstructing the functional imaging data into a volume image representation;
thresholding transverse slices of the volume image representation according to a maximum pixel intensity of each corresponding slice;
determining a cluster of the thresholded slices which correspond to a left ventricle;
cleaning the determined cluster of slices according to a predetermined Manhattan distance between a left ventricle centroid in a central slice to the left ventricle centroid in the remaining clustered slices; and
isolating the left ventricle in the cleaned slices according to cardiac angles of a septum of the myocardium; and
a display apparatus configured to display the isolated left ventricle.

* * * * *